United States Patent [19]

Kelman

[11] Patent Number: 4,605,409

[45] Date of Patent: Aug. 12, 1986

[54] INTRAOCULAR LENS WITH MINIATURE OPTIC HAVING EXPANDABLE AND CONTRACTIBLE GLARE-REDUCING MEANS

[76] Inventor: Charles D. Kelman, North Shore Towers - 269 Grand Central Pkwy., Bldg. 3, Floral Park, N.Y. 11005

[21] Appl. No.: 612,584

[22] Filed: May 21, 1984

[51] Int. Cl.$^4$ .................................................. A61F 2/16
[52] U.S. Cl. ..................................................... 623/6
[58] Field of Search ........................... 3/13, 1; 623/6

[56] References Cited

U.S. PATENT DOCUMENTS

| | | | |
|---|---|---|---|
| 4,056,855 | 11/1977 | Kelman | 3/13 |
| 4,168,547 | 9/1979 | Konstantinov et al. | 623/6 |
| 4,172,297 | 10/1979 | Schlegel | 3/13 |
| 4,402,579 | 9/1983 | Poler | 3/13 |
| 4,435,856 | 3/1984 | L'Esperance | 3/13 |
| 4,450,593 | 5/1984 | Poler | 3/13 |
| 4,535,488 | 8/1985 | Haddad | 623/6 |

*Primary Examiner*—Ronald L. Frinks
*Attorney, Agent, or Firm*—Henry Sternberg; Bert J. Lewen

[57] ABSTRACT

An intraocular lens having an optic of sufficiently small dimension so as to permit its insertion through an incision substantially smaller than 5 mm in length. The lens includes a masking means which is deformable between an expanded condition in which it masks the edge portion of the optic which would otherwise cause a glare effect and a contracted condition in which the masking means is located within the confines of said small dimension of the optic.

22 Claims, 8 Drawing Figures

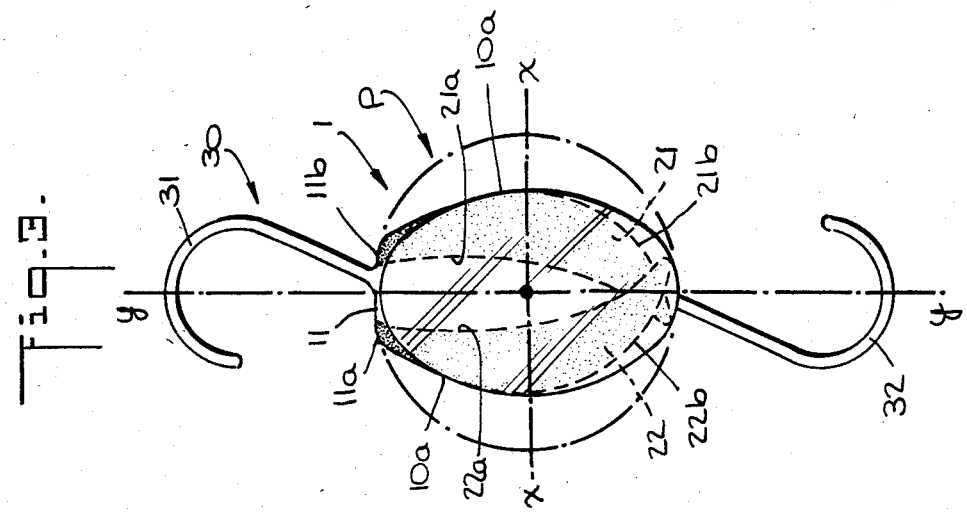
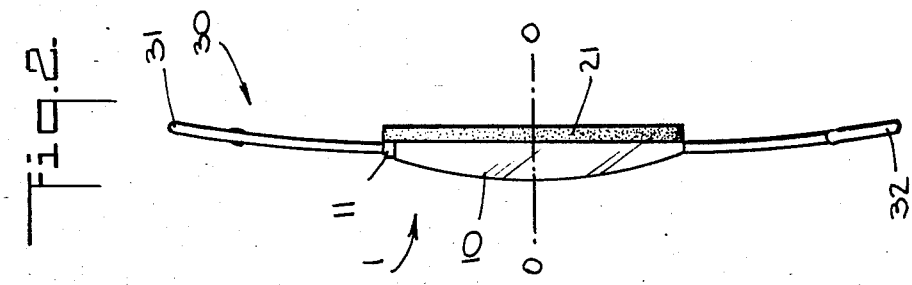
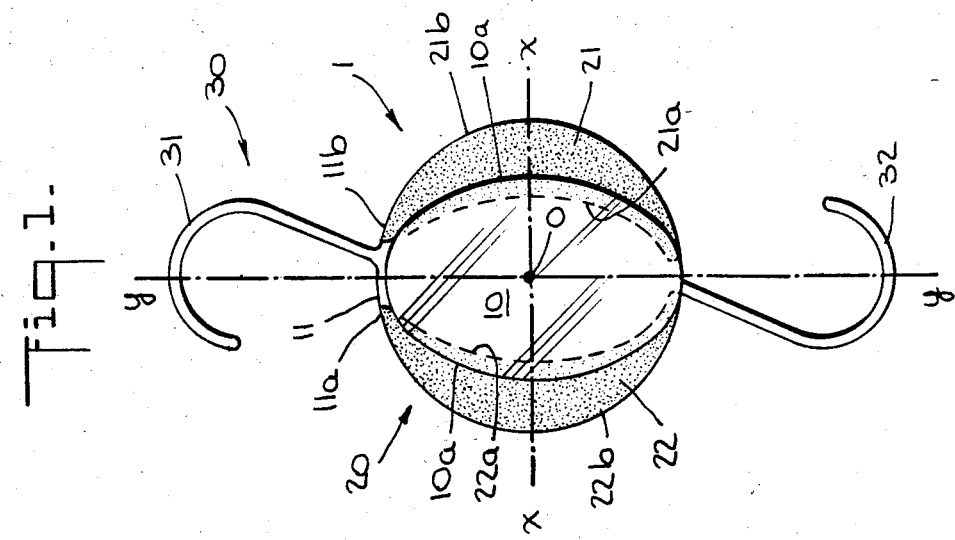

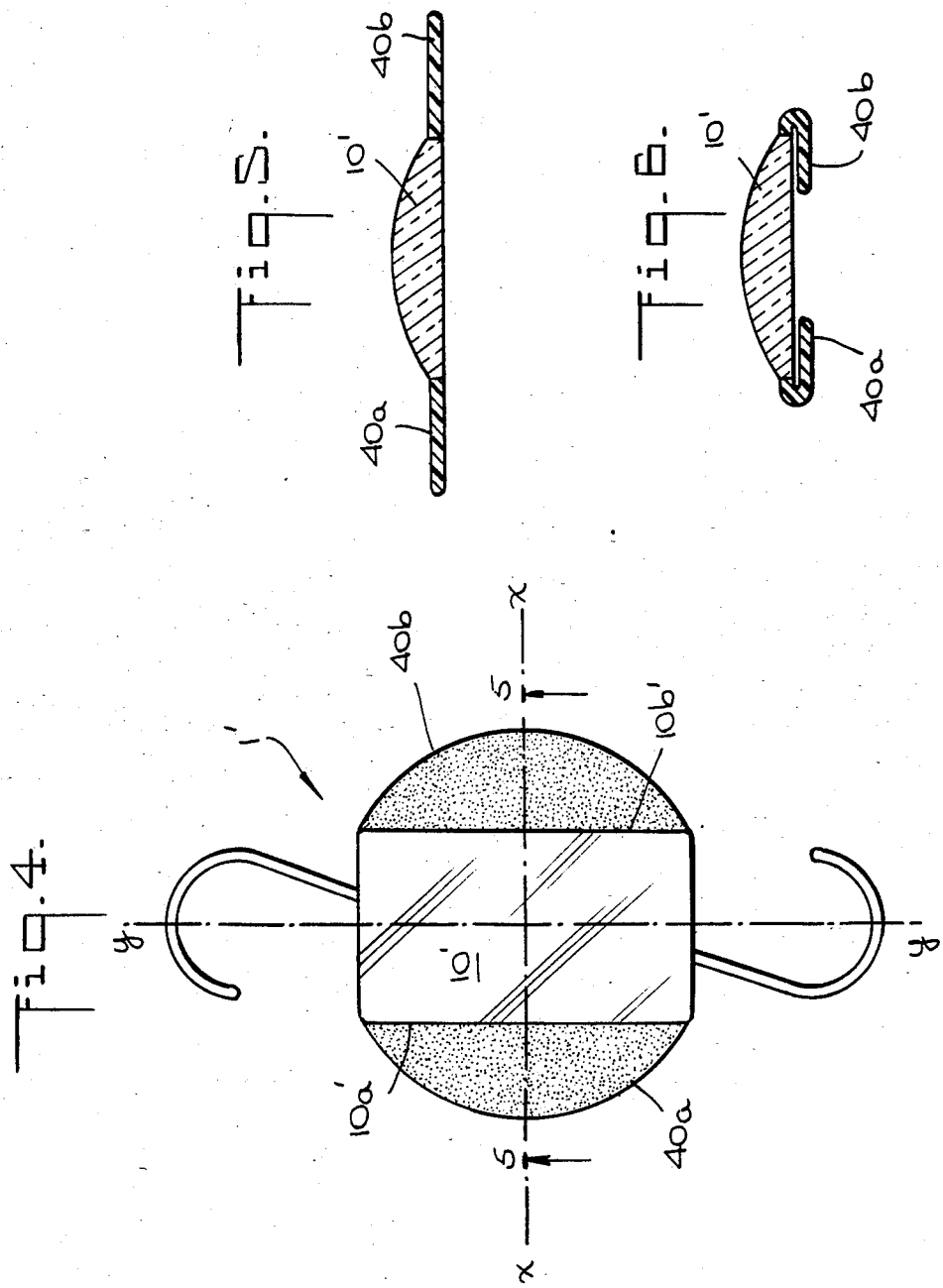

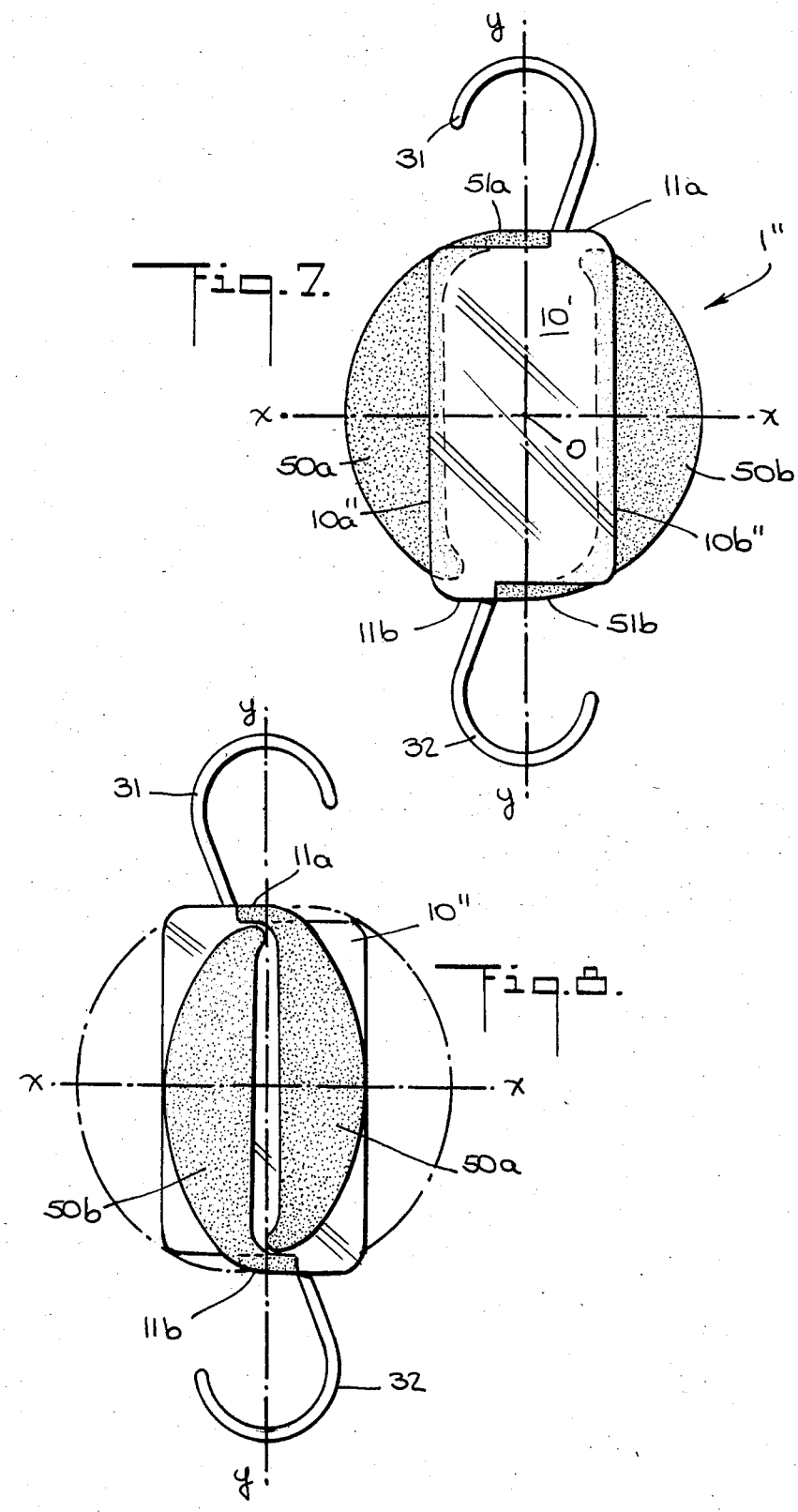

INTRAOCULAR LENS WITH MINIATURE OPTIC HAVING EXPANDABLE AND CONTRACTIBLE GLARE-REDUCING MEANS

This invention relates to intraocular lenses for the human eye, and, more particularly, to intraocular lenses of the type which can be positioned in the anterior chamber, the posterior chamber, or partially in the anterior chamber and partially in the posterior chamber of the eye. The invention also relates to methods of inserting such lenses in a eye.

One type of intraocular lens is described and claimed in my U.S. Pat. No. 4,253,200 issued Mar. 3, 1981. Such a lens is inserted into the eye through a corneo-scleral incision that may be also used to remove a natural lens. To minimize the possibility of injury to the eye, it is important that the incision be made as small as possible. According to that patent the size of the incision is dependent nearly entirely on the diameter of the optic. In order to further reduce the size of the incision, therefore, the size of the optic would have to be reduced. This can be accomplished in several ways. First, the optic may be made in the form of a twopiece optic, allowing the surgeon to make an incision in the eye smaller than the diameter of the lens body, or optic, and inserting the two parts of the optic separately through the incision. In the case of the two-piece optic, depending on where the optic is split and depending on the means used for connecting the two pieces together there may result, in some instances, an undesirable glare effect at the juncture of the two pieces. A second possibility is to form the lens with an optic of reduced size, at least in the one dimension thereof which must pass through the incision. However, the undesirable glare effect described above has in the past also precluded the use of such optics which were substantially smaller than 5 mm in diameter, or at least had one dimension (transverse to the optical axis) of such substantially smaller size. The reason was that some of the light rays entering the eye would impinge on the peripheral marginal regions of such miniature optic which, because of the small dimensions involved, are located in the path of such light rays and would scatter the rays toward the retina.

A further possibility is to form the optic out of a flexible material such as silicone and to curl the optic into the shape of a small cylinder which can then be readily inserted into a small incision. This latter construction requires that the curled optic fully assumes its flat initial shape after it is inserted into the eye. Any deviation from such flat shape would result in optical distortion.

Also, if the material used for such flexible optic is silicone, materials in the eye, such as, for example, fibrin, may collect on the optic due to the surface characteristics of silicone. It is therefore preferred to make the optic out of a material such as polymethylmethacrylate (PMMA) which is not only relatively rigid but also does not have properties which cause any of the materials in the eye to adhere thereto. PMMA's physical properties are such that fibrin and other materials in the eye are constantly washed away from its surface rather than adhering thereto.

It is an object of the present invention, therefore, to provide a new and improved intraocular lens which avoids one or more of the limitations of prior such lenses.

It is another object of the invention to provide a new and improved intraocular lens which has a lens body which is smaller, in at least one transverse dimension thereof, than the lens body of conventional lenses, yet which does not result in undesirable glare.

Glare effect is produced whenever there is located, in the path of the light rays which pass through the pupil to the retina, an edge or similar boundary between regions which are both substantially transparent as distinguished from one being substantially opaque. For example, glare effect will result if a lens body is split into two parts along, e.g. a diameter, or if an optic has a 3 mm diameter while the bundle of light rays passing through the pupil has a transverse cross sectional area which is 6mm in diameter, since the outermost rays will pass through the optically transparent fluid in the eye while the innermost rays pass through the optic. No such edge glare results however in those cases in which one side of the edge or boundary in question is masked, i.e. is opaque, such as for example, the boundary formed by the iris at its inner edge defining the pupil. The opaque iris thus masks without causing glare effect.

In accordance with the invention an intraocular lens comprises a lens body and a position-fixation means extending from the lens body for fixating the lens body within the eye. The lens body is of minature size, i.e. it has at least one dimension sufficiently small in size to permit the lens to be inserted into the eye through an incision which is substantially smaller than the incision now generally required for insertion of conventional lenses. The lens also includes a deformable masking means integral with the lens body for preventing glare-effects when the masking means is in expanded condition. For insertion, the masking means are deformable into a contracted condition in which they pass, together with the lens body, through the desired substantially smaller incision.

In accordance with the invention an intraocular lens comprises a lens body for focusing light rays on the retina of an eye, the lens body has a pair of imaginary coordinate axes at right angles to one another and to the optical axis and has a maximum dimension of substantially less than 5 mm along any line drawn through the lens body parallel to a given one of its pair of coordinate axes, said maximum dimension being defined by a pair of opposite peripheral edge portions of the lens body transverse to said one coordinate axis and located apart a distance equal to said maximum dimension, and masking means integrally connected with the lens body and deformable between an expanded condition in which the masking means has a first portion thereof adjacent one of said peripheral edge portions of said lens body and a second portion thereof spaced from and located radially outwardly of said one peripheral edge portion of said lens body for inhibiting light rays which are directed toward said peripheral edge portion from being scattered thereby toward the retina after the lens has been implanted in an eye, and a contracted condition in which said masking means are located substantially entirely within said maximum dimension of said pair of opposite peripheral edge portions of said lens body for permitting insertion of said lens through an incision in an eye which is substantially less than 5 mm in length.

For a better understanding of the present invention, together with other and further objects thereof, reference is made to the following description, taken in connection with the accompanying drawings, and its scope will be pointed out in the appended claims.

Referring now to the drawings:

FIG. 1 is a front elevational view of the intraocular lens embodying a preferred form of the present invention with the masking means in normal expanded condition thereof;

FIG. 2 is a side elevational view of the intraocular lens represented in FIG. 1;

FIG. 3 is a front elevational view of the intraocular lens represented in FIGS. 1 and 2 showing the masking means in contracted condition;

FIG. 4 is a front elevational view similar to the view in FIG. 1, of another embodiment of a lens constructed in accordance with the invention showing the masking means in normal expanded condition;

FIG. 5 is a transverse sectional view along line 5—5 of FIG. 4;

FIG. 6 is a transverse sectional view similar to the view in FIG. 5 showing the masking means in contracted condition thereof;

FIG. 7 is a front elevational view of an intraocular lens according to still another embodiment of the invention and showing the masking means thereof in expanded condition;

FIG. 8 is a rear elevational view of the intraocular lens of FIG. 7 in contracted condition thereof.

Referring now particularly to FIGS. 1, 2 and 3 of the drawings, reference numeral 1 generally indicates an intraocular artificial lens according to the preferred embodiment of the present invention. The lens 1 can be formed of any suitable material compatible with the environment of the human eye, such as a non-toxic plastic, for example, polymethylmethacrylate.

The lens 1 includes a medial light focusing lens body, or optic 10, having, for example, a convex anterior surface and a generally flat posterior surface and having a pair of imaginary coordinate axes "x" and "y" perpendicular to each other and to the optical axis "o" of the lens body 10. While optics of conventional intraocular lenses are generally round and approximately five to six millimeters in diameter, the lens body 10, according to the present invention, may be of any suitable shape, for example, round, oval or rectangular, but has a maximum dimension, in the direction of at least one of said coordinate axes, of substantially less than 5mm, i.e. substantially less than the corresponding dimension of a conventional intraocular lens optic. According to the present invention the lens 1 further includes position-fixation means 30 having a pair of opposed curved position-fixation members 31, 32 which are preferably resilient filaments of polymethylmethacrylate, or similar material, integrally connected with the lens body.

The lens body 10 is preferably oval and is elongated along the Y—Y axis and the position-fixation members 31, 32 are preferably connected to opposite ends of such elongated lens body so as to extend generally in the direction of the Y—Y axis.

The lens 1 further includes a masking means 20 which in the preferred embodiment shown in FIGS. 1, 2 and 3 is in the form of a pair of wing members 21 and 22. These wing members are preferably elongated and preferably integrally connected at one end thereof to a connecting stem portion 11 which in turn is integrally connected with the lens body 10 at one of the longitudinal ends of that lens body. The wing members 21 and 22 are generally planar and are located in a plane which, as best seen in FIG. 2, is parallel to and closely adjacent to the plane of the lens body 10. Preferably, this is accomplished by forming the connecting stem 11 so that the latter extends both generally radially outwardly of the lens body 10 and posteriorly thereto beyond the posterior surface thereof. The wing members 21, 22 can thus be moved in sliding relation with respect to the flat posterior surface of the lens body 10.

According to the preferred embodiment of the present invention, the wing members 21, 22 are resiliently connected to the lens body 10 at the stem 11. Thus, the wing members 21, 22 are deformable with respect to the lens body 10 between an expanded condition seen in FIG. 1 and a contracted condition seen in FIG. 3. The wing members 21, 22 preferably have inner marginal edges 21a and 22a, respectively, which, in the normal expanded condition thereof, seen in FIG. 1, are located slighly, e.g. ¼ mm inwardly of the opposed transverse marginal peripheral edges 10a of the lens body 10. The wing members thus overlap the opposed transverse peripheral edges 10a, i.e. those edges which are transverse to the X—X coordinate axis.

Wing members 21, 22, which form the masking means, are preferably optically opaque so as to inhibit light rays which would otherwise impinge upon the transverse peripheral edges 10a of the lens body, from being scattered by those peripheral edges to the retina of the eye to cause a glare effect. The outer marginal edges 21b, 22b, respectively, of wing members 21, 22 extend in expanded condition of the masking means to and preferably slightly beyond the perimeter of an imaginary circle P (see FIG. 3) of about 5 mm in diameter, which represents the size of the area desired to be covered. This area is covered in part by the lens body 10 and in remaining part by the masking means 20. The latter being of such size and shape as to accomplish that result.

By exerting a compressive force on the wing members 21, 22 they may be swivelled from the FIG. 1 to the FIG. 3 position thereof, so that even the outermost edges 21b and 22b thereof will be located within the maximum X—X dimension of the lens body 10. This permits the lens 1 to be inserted through an incision in the cornea which is no greater than would be required for the insertion of the lens body 10 alone in the direction parallel to the "y" axis thereof and which is therefore substantially smaller than the incision which is required for currently known intraocular lenses of this type.

It will be seen, that in order to swivel the wing members 21, 22 from the FIG. 1 to the FIG. 3 position thereof, an external force must be applied either by the surgeon placing and thereafter maintaining the wing members in the contracted condition with his surgical tools during insertion into the eye, or by use of a suture, not shown, maintaining the members in the condition seen in FIG. 3. In either event, upon release of the external force the wing members will automatically be returned by the resilient connections 11a, 11b at stem 11, to the expanded condition thereof seen in FIG. 1, in which condition they will remain after seating of the lens in the eye. It will be seen that, according to this embodiment of the invention, the wing members 21, 22 overlie the lens body 10 either only partially, when in the FIG. 1 expanded condition or substantially in their entirety, when in the contracted FIG. 3 condition. According to the preferred embodiment, the entire lens 1 may be of one-piece construction and may be of polymethylmethacrylate material. Once the material is fixed, the resiliency of the wing members can be controlled by the shape and thickness of the ends 11a, 11b of the individual wing members in the region thereof connected to the stem 11. Preferably the structure is formed such that the resilient connection at stem 11 will provide a memory which, upon release of the external force, will return the wing members 21, 22 to their normal expanded position seen in FIG. 1. In such one-piece construction, the opacity of the wing members 21, 22 is preferably achieved by leaving the flat surfaces of the wing members in rough, unground, condition. Alternatively, one of the surfaces of the wing members may be coated with an opaque coating.

Referring now more particularly to FIGS. 4, 5 and 6 there is shown another embodiment of the present invention. The lens 1' of FIGS. 4, 5 and 6 has a lens body 10' of rectangular shape, though it will be understood that it could also be of elliptical, or even of round shape. However, the elliptical or rectangular shape is preferred since such optics permit more light to enter the eye through the optic when the pupil is dilated, as for example for night vision. Since under normal light conditions, a pupil size of less than about 3 mm diameter is to be expected, a 3 mm diameter optic will be appropriate. Under poor light conditions, on the other hand, the pupil may dilate to about 5 mm in diameter. It is therefore preferred to have an elongated optic which while narrow in width will, at least along the length thereof, accommodate as much of the available light as possible under poor light conditions. According to this embodiment of the invention the masking means is in the form of a pair of sheet members 40a, 40b. As best seen in FIG. 5 these sheet members 40a, 40b are preferably flat and preferably of soft resilient material such as silicone bonded edge-to-edge to the elongated peripheral edges 10a', 10b' of the lens body 10' and thus overlying such peripheral edges. When reference is made herein to the masking means overlying portions of the periphery of the lens body, it is intended to include not only those structures in which the masking means is located anteriorly or posteriorly of the lens body but also those structures in which the masking means is located radially outwardly of the lens body, i.e. in edge-to-edge adjacency, as for example, in the lens of FIGS. 4, 5 and 6. Thus, the masking means 40a, 40b according to this latter embodiment, are substantially coplanar with the lens body 10' and, since they are of flexible sheet material, can be resiliently deformed into the condition thereof shown in FIG. 6, i.e., folded under the lens body 10' so as to overlie substantially in their entirety the posterior surface of the lens body 10'. Upon removal of the external force maintaining the masking means 40 in the condition shown in FIG. 6, the resilient nature of the masking means 40 will return the latter to the expanded condition thereof shown in FIGS. 4 and 5.

Whether the masking means are in the form of a pair of wing members as seen in FIGS. 1, 2 and 3 or in the form of a pair of sheet members as seen in FIGS. 4, 5 and 6, or in another form, it is important that the transverse peripheral edges 10a and 10b of the lens body 10 and the transverse peripheral edges 10a' and 10b' of lens body 10' are not left free to scatter light rays. Either they are covered by the wing members 21, 22 overlying them anteriorly or posteriorly, such as seen in FIGS. 1, 2, and 3, or they are covered by having directly bonded to them, edge-to-edge, a resilient sheet material such as shown in FIGS. 4, 5 and 6 in which event the masking means overlie the edge portion by being outwardly adjacent thereto. In either event, the glare effect which would result from light rays impinging on the transverse peripheral edges 10a and 10b, or 10a' and 10b' of the miniature optic 10 or 10' respectively and being thereby scattered toward the retina, is inhibited by the provision of an artificial iris in the form of the masking means shown.

It will be seen that in accordance with the present invention the lens 1' may alternatively be of round shape (not shown) and have a round ring-shaped masking means of a soft resilient material fully surrounding it.

The preferred lens body, according to the present invention, has a maximum dimension along any line therethrough in a direction parallel to a given one of the said pair of coordinate axes, of about 3 mm. For example, the dimension along the X axis of optic 10' in FIG. 4 may be about 3 mm and the dimension along the Y axis may be about 6 mm. This will provide the additional light needed for better night vision without increasing that dimension of the lens which controls the size of the incision, i.e., in this case, the "X" dimension. It will be seen that the masking means need only be provided in connection with the peripheral edges substantially transverse to the "X" axis, i.e. edges 10a and 10b for the FIG. 1 embodiment and 10a' and 10b' for the FIG. 4 embodiment and need not be provided along the marginal regions at the top and bottom of the elongated optic. As a consequence of the elongated shape of the optic, the only marginal edges which will normally be within the bundle of light rays impinging on the retina through the pupil of the eye and therefore the only edges which need to be masked are the transverse peripheral edges such as edges 10a', 10b' in FIG. 4.

In FIG. 7 there is shown still another embodiment of the present invention. Lens 1" in FIG. 7 has a rectangular optic 10" identical to the optic 10' in FIG. 4 except that optic 10" is provided with a pair of stems 11a and 11b extending at opposite elongated ends thereof. Position-fixation members 31, 32 preferably extend from the stems 11a and 11b as shown and may be formed as onepiece with the lens body 10". The masking means 50a, 50b according to the FIG. 7 embodiment are substantially identical to the masking means 20 in FIG. 1 except that instead of the wing members 50a and 50b being connected to a single stem 11, they are each connected to a different one of the stems 11a and 11b spaced from each other along the Y axis at opposite ends of lens body 10" and situated generally intermediate the transverse edge portions 10a" and 10b" of lens body 10". Elongated wing member 50a is integrally connected at one end thereof with stem 11a while elongated wing member 50b is integrally connected at one end thereof with stem 11b. The stems 11a, 11b, the connecting portions 51a, 51b and the wing members 50a, 50b are all part of the masking means and are shaped so as to cover that part of the imaginary circle P (which circle represents a transverse cross-sectional area of about 6 mm) which is not covered by the lens body 10". As is the case with the embodiment of FIGS. 1, 2 and 3, the wing members 50a, 50b are deflectable into the contacted condition of FIG. 8 by sliding under the posterior surface of lens body 10" so that the outer maximum dimension of any line drawn through the lens 1" in a direction parallel to the X axis will be no greater than the maximum X dimension of the lens body 10". The connecting portions 51a, 51b are sufficiently thin so as to permit the wing members 50a, 50b to flex from the expanded condition thereof in FIG. 7 to the contracted condition in FIG. 8.

From the foregoing description it will be apparent that an intraocular lens constructed in accordance with the invention has the advantage that the lens can be inserted into the eye through an incision which is smaller than the incisions currently required for conventional intraocular lenses. It should be noted that currently the incision must be at least 5 mm in length as determined by the minimum size optic in conventional use. Since incisions of only approximately 2.5 mm to 3 mm is length are required to remove the cataracted natural lens it is of course highly desirable to have an intraocular lens which will not require a larger incision.

While there have been described what are at present considered to be the preferred embodiments of this invention, it would be obvious to those skilled in the art that various changes and modifications may be made therein without departing from the invention, and it is, therefore, aimed to cover all such changes and modifications as fall within the true spirit and scope of the invention.

What is claimed is:

1. An intraocular lens comprising:
   a lens body for focusing light rays on the retina of an eye, said lens body having an anterior and a posterior face and having a pair of imaginary coordinate axes at right angles to one another and to the optical axis and said lens body having a maximum dimension of substantially less than 5 mm along any line drawn through said lens body parallel to a given one of its pair of coordinate axes, said maximum dimension being defined by a pair of opposite peripheral edge portions of said lens body transverse to said one coordinate axis, and
   masking means including a pair of wing portions operatively connected with said lens body for sliding movement along a face of said lens body between an expanded condition in which free inner edge portions of said wing portions are respectively located adjacent said peripheral edge portions of said lens body and said wing portions extend radially outwardly of said peripheral edge portions of said lens body for inhibiting light rays which are directed toward said peripheral edge portions from being scattered thereby toward the retina after the lens has been implanted in an eye, and a contracted condition in which said pair of wing portions are located substantially entirely within said maximum dimension of said pair of opposite peripheral edge portions of said lens body for permitting insertion of said lens through an incision in an eye which is substantially less than 5 mm in length.

2. An intraocular lens according to claim 1 in which said masking means comprises resiliently deformable connecting means connecting said wing portions to said lens body for sliding movement of said wing portions from said expanded to said contracted condition thereof by application of an external force and for returning said wing portions substantially to their expanded condition upon removal of said external force.

3. An intraocular lens according to claim 1, in which each said wing portion is integrally connected with said lens body at substantially a single point located on a portion of said lens body other than at said opposite peripheral edge portions.

4. An intraocular lens according to claim 1 in which said lens body has a generally elliptical periphery and said maximum dimension is the minor axis of the ellipse.

5. An intraocular lens according to claim 1 in which said lens body is generally rectangular and said maximum dimension is the shorter dimension of the rectangle.

6. An intraocular lens according to claim 1 in which said maximum dimension is about 3 mm.

7. An intraocular lens according to claim 5 in which said shorter dimension is about 3 mm and the longer dimension of said substantially rectangular lens body is about 6 mm.

8. An intraocular lens according to claim 1 further comprising position-fixation means connected with said lens body for seating said lens in the eye.

9. An intraocular lens according to claim 1 in which said lens body has a maximum dimension in a direction parallel to the other of its coordinate axes which is substantially greater than said first mentioned dimension.

10. An intraocular lens according to claim 1 in which said masking means comprises optically opaque means.

11. An intraocular lens comprising:
    a lens body for focusing light rays on the retina of an eye, said lens body having a pair of imaginary coordinate axes at right angles to one another and to the optical axis and said lens body having a maximum dimension of substantially less than 5 mm along any line drawn through said lens body parallel to a given one of its pair of coordinate axes, said maximum dimension being defined by a pair of opposite peripheral edge portions of said lens body transverse to said one coordinate axis and located apart a distance equal to said maximum dimension, and
    a pair of wing portions each having a free inner marginal edge portion and an outer marginal edge portion, said wing portions slideable with respect to said lens body between an expanded condition in which said free inner marginal edge portions thereof are located respectively adjacent said pair of peripheral edge portions of said lens body and said outer marginal edge portions thereof, are respectively spaced from and located radially outwardly of said peripheral edge portions of said lens body for inhibiting light rays which are directed toward said peripheral edge portions from being scattered thereby toward the retina after the lens has been implanted in an eye, and a contracted condition in which said free inner marginal edge portions are at second locations inwardly of said first mentioned locations thereof and said wing portions are located substantially entirely within said maximum dimension of said pair of opposite peripheral edge portions of said lens body for permitting insertion of said lens through an incision in an eye which is substantially less than 5 mm in length.

12. An intraocular lens according to claim 11 in which said pair of wing portions are at least in said contracted condition thereof, located entirely in a plane parallel and adjacent to the plane of said lens body, said wing portions adapted to substantially overlie in their entirety said lens body when said masking means is in said contracted condition and said lens comprising resilient means connecting said wing portions to said lens body for resiliently slideably returning said wing portions to their expanded condition upon release of external forces holding said wing portions in contracted condition.

13. An intraocular lens according to claim 12 in which each of said pair of wing portions is swivellably connected with said lens body at a peripheral region of said lens body intermediate the aforesaid pair of peripheral portions of said lens body.

14. An intraocular lens according to claim 13 in which said wing portions are connected to said lens body through a stem portion extending generally radially with respect to said lens body only at said intermediate peripheral region thereof, said swivellable connection including resilient means for returning said wing portions to their initial expanded condition when the externally applied force is removed.

15. An intraocular lens according to claim 13 in which said wing portions have inner edges corresponding generally to the shape of said transverse peripheral edge portions of said lens body and said inner edges being located slighly inwardly of and overlying said peripheral edge portions of said lens body when said masking means is in said expanded condition.

16. An intraocular lens according to claim 15 in which said lens body is of oval shape and includes a stem at one longitudinal end thereof, each said wing portion being elongated and resiliently connected at only one end thereof to said stem and each said wing portion having an inner curved edge generally corresponding to the curvature of the marginal peripheral portion of said lens body which it overlies.

17. An intraocular lens according to claim 11 in which said lens body covers an area, in a plane perpendicular to the optical axis of the lens body, which is smaller than the area within an imaginary circle, in said plane, of 5 mm diameter centered on the optical axis, said masking means being shaped and dimensioned such as to substantially cover the remaining area within said imaginary circle when said masking means are in said expanded condition thereof.

18. An intraocular lens according to claim 12 in which said wing portions are of generally elongated shape, each having a pair of opposite end portions, and each wing portion connected only at one of its ends to said lens body.

19. An intraocular lens according to claim 18 in which said lens body is of elongated shape, said transverse peripheral edge portions extending generally in the direction of elongation of said lens body and said lens body including a stem portion extending from one end thereof, each said wing portion being connected to said stem portion.

20. An intraocular lens according to claim 18 in which said lens body is of elongated shape, said transverse peripheral edge portion extending generally in the direction of elongation of said lens body and said lens body including a pair of stem portions extending from opposite ends, respectively, of said lens body each said wing portion being connected to an opposite one of said pair of stem portions respectively.

21. An intraocular lens according to claim 17 in which said opposite peripheral edge portions of said lens body are subtended by and lie substantially within said imaginary circle and said first portions of said masking means are adjacent to said opposite peripheral edge portions along the entire length of the latter lying within said imaginary circle.

22. An intraocular lens comprising:
a lens body for focusing light rays on the retina of an eye, said lens body having a pair of imaginary coordinate axes at right angles to one another and to the optical axis and having a length along one coordinate axis substantially greater than the width thereof along the other of said coordinate axes,
position-fixation means cooperating with said lens body for seating said lens body in the eye,
a pair of generally planar wing portions having free inner edge portions, said pair of wing portions being relatively slidable with respect to said lens body along a plane generally parallel to the plane of said lens body, and
connecting means for connecting said wing portions to said lens body for sliding movement with respect to said lens body between an expanded condition in which said free inner edge portions of said wing portions cooperate with opposed portions of the periphery of said lens body which are transverse to said other coordinate axis, to inhibit glare which would result from light rays being deflected by said opposed portions, and a contracted condition in which said free inner edge portions of said pair of wing portions are located substantially further inwardly of said opposed portions and said wing portions are located substantially entirely within said width dimension of said lens body, to allow insertion of the lens through an incision no greater than the minimum size incision required for insertion in lengthwise direction of a lens body having said width.

* * * * *

UNITED STATES PATENT AND TRADEMARK OFFICE
CERTIFICATE OF CORRECTION

PATENT NO. : 4,605,409

DATED : August 12, 1986

INVENTOR(S) : CHARLES D. KELMAN

It is certified that error appears in the above-identified patent and that said Letters Patent is hereby corrected as shown below:

Column 9, line 10, after "body" insert --only--.

Signed and Sealed this

Eleventh Day of November, 1986

Attest:

DONALD J. QUIGG

*Attesting Officer*   *Commissioner of Patents and Trademarks*